(12) United States Patent
Hino et al.

(10) Patent No.: US 9,238,610 B2
(45) Date of Patent: Jan. 19, 2016

(54) METHOD FOR PURIFYING METHACRYLIC ACID

(71) Applicant: MITSUBISHI RAYON CO., LTD., Tokyo (JP)

(72) Inventors: Tomomichi Hino, Hiroshima (JP); Shinpei Kato, Hiroshima (JP); Hideyuki Sonobe, Hiroshima (JP); Manabu Hoshino, Hiroshima (JP)

(73) Assignee: MITSUBISHI RAYON CO., LTD., Tokyo (JP)

( * ) Notice: Subject to any disclaimer, the term of this patent is extended or adjusted under 35 U.S.C. 154(b) by 0 days.

(21) Appl. No.: 14/366,673

(22) PCT Filed: Dec. 26, 2012

(86) PCT No.: PCT/JP2012/083599
§ 371 (c)(1),
(2) Date: Jun. 18, 2014

(87) PCT Pub. No.: WO2013/103112
PCT Pub. Date: Jul. 11, 2013

(65) Prior Publication Data
US 2014/0364646 A1    Dec. 11, 2014

(30) Foreign Application Priority Data

Jan. 5, 2012  (JP) ................. 2012-000547

(51) Int. Cl.
| | | |
|---|---|---|
| *C07C 51/43* | (2006.01) | |
| *C07C 51/44* | (2006.01) | |
| *C07C 51/48* | (2006.01) | |
| *C07B 63/00* | (2006.01) | |

(52) U.S. Cl.
CPC ............... *C07C 51/43* (2013.01); *C07B 63/00* (2013.01); *C07C 51/44* (2013.01); *C07C 51/48* (2013.01)

(58) Field of Classification Search
None
See application file for complete search history.

(56) References Cited

FOREIGN PATENT DOCUMENTS

| | | |
|---|---|---|
| JP | 2003-126607 | 5/2003 |
| JP | 3559523 | 9/2004 |
| JP | 2009-184982 | 8/2009 |
| JP | 2012-102129 | 5/2012 |
| WO | 99/06348 | 2/1999 |

OTHER PUBLICATIONS

The Society of Chemical Engineering, "Crystallizer and Design Method Thereof", Chemical Engineering Handbook, Revised, Sixth Edition, Feb. 1999, p. 489-p. 523, Maruzen Publishing Co., Ltd., with partial translation thereof.
Chuzo Shimizu, "Purification of Organic Compound by Kureha Continuous Crystal Purifier", Chemical Engineering, Dec. 1982, p. 49, vol. 27, Issue 3, with English translation thereof.
"International Search Report (Form PCT/ISA/210)", mailed on Mar. 12, 2013, with English translation thereof, p. 1-p. 2.

*Primary Examiner* — Yevegeny Valenrod
(74) *Attorney, Agent, or Firm* — Jianq Chyun IP Office

(57) ABSTRACT

Provided is a crystallization method by which a highly-pure methacrylic acid crystal can be produced with high productivity. The method for purifying methacrylic acid according to the present disclosure involves using crude methacrylic acid having a maleic acid concentration of 2000 ppm by mass or less and an acrylic acid concentration of 2000 ppm by mass or less and setting the slurry temperature to −10 to 10° C. in order to crystallize methacrylic acid. A suspension-type jacket-cooling-system crystallization vessel is used as the crystallization apparatus, and an absolute value of the difference between a crystallization temperature and a temperature of a cooling medium in the jacket is preferably 15° C. or less.

7 Claims, 2 Drawing Sheets

METHOD FOR PURIFYING METHACRYLIC ACID

CROSS-REFERENCE TO RELATED APPLICATION

This application is a 371 application of an international PCT application serial no. PCT/JP2012/083599, filed on Dec. 26, 2012, which claims the priority benefit of Japan application no. 2012-000547, filed on Jan. 5, 2012. The entirety of each of the above-mentioned patent applications is hereby incorporated by reference herein and made a part of this specification.

TECHNICAL FIELD

The present invention relates to a method for purifying methacrylic acid.

BACKGROUND ART

Methacrylic acid is obtained by oxidizing isobutylene, tert-butyl alcohol, methacrolein, or isobutyl aldehyde through single-stage or two-stage catalytic gas-phase oxidation reactions in the presence of molecular oxygen. In addition to the desired methacrylic acid (boiling point of 161° C./760 mmHg, melting point of 15° C.), the following byproducts are also included in the obtained product: carboxylic acids such as formic acid, acetic acid, propionic acid, maleic acid, citraconic acid, benzoic acid, toluic acid, terephthalic acid, and acrylic acid; and aldehydes such as formaldehyde, acetaldehyde, propionaldehyde, methacrolein, benzaldehyde, tolualdehyde, furfural, and the like. Most of those impurities can be isolated and purified by generally used purification methods such as distillation and extraction. However, trace impurities such as aldehydes are hard to remove. Since aldehydes absorb light in the ultraviolet region, coloration may occur in a methacrylic acid product in which not a small amount of aldehyde remains. To avoid such coloration, it is necessary to reduce as much of the remaining amount of the aldehyde as possible. Under such circumstances, crystallization methods have been studied to obtain methacrylic acid which is more highly purified than that obtained by distillation methods.

Patent Literature 1 describes the following method for producing purified methacrylic acid: methacrylic acid is crystalized in a solution prepared by adding a second component such as methanol, ethanol, propanol or butanol to crude methacrylic acid, and the deposited crystals are isolated from the mother liquor.

Patent Literature 2 describes the following method: when crystals are to be deposited by a cooling crystallization method using a condenser equipped with an external circulation device or a jacket device to exchange heat through the heat transfer surface of the condenser, crystals (scales) grow on the heat transfer surface and lower the cooling capability. Considering such situations, a change in the operational conditions of the crystallization device, a switch of condensers, a change in the conditions for reactivation treatment of the condenser and the like are proposed in the method.

REFERENCE LIST

Patent Literature

Patent Literature 1: JP 3559523
Patent Literature 2: JP 2003-126607 A

SUMMARY OF THE INVENTION

Technical Problem

However, using the method described in Patent Literature 1, despite the operational conditions of the crystallization device controlled according to a predetermined controlling standard, the amount of methacrylic acid crystals may decrease, thereby lowering the productivity of the crystallization device. To counteract such circumstances, when a cooling crystallization method in Patent Literature 2 above is used, the cooling capacity of the device is usually increased so as to recover the production level. However, when the cooling capacity is increased, there is also an increase in the frequency of switching condensers or of performing reactivation treatment on the condenser as scaling on the cooling surface accelerates, and productivity may further be lowered.

The present invention was carried out in consideration of the above problems. Its objective is to provide a crystallization method capable of producing highly purified methacrylic acid crystals with high productivity.

Solution to the Problem

In a method for purifying methacrylic acid according to an embodiment of the present invention, crystallization of methacrylic acid is performed by using crude methacrylic acid as a raw material with a maleic acid concentration of no greater than 2000 ppm by mass and an acrylic-acid concentration of no greater than 2000 ppm by mass while setting a slurry temperature at −10~10° C.

Effects of the Invention

An embodiment of the present invention provides a crystallization method capable of producing highly purified methacrylic acid crystals with high productivity.

DESCRIPTION OF EMBODIMENTS

Figure 1:
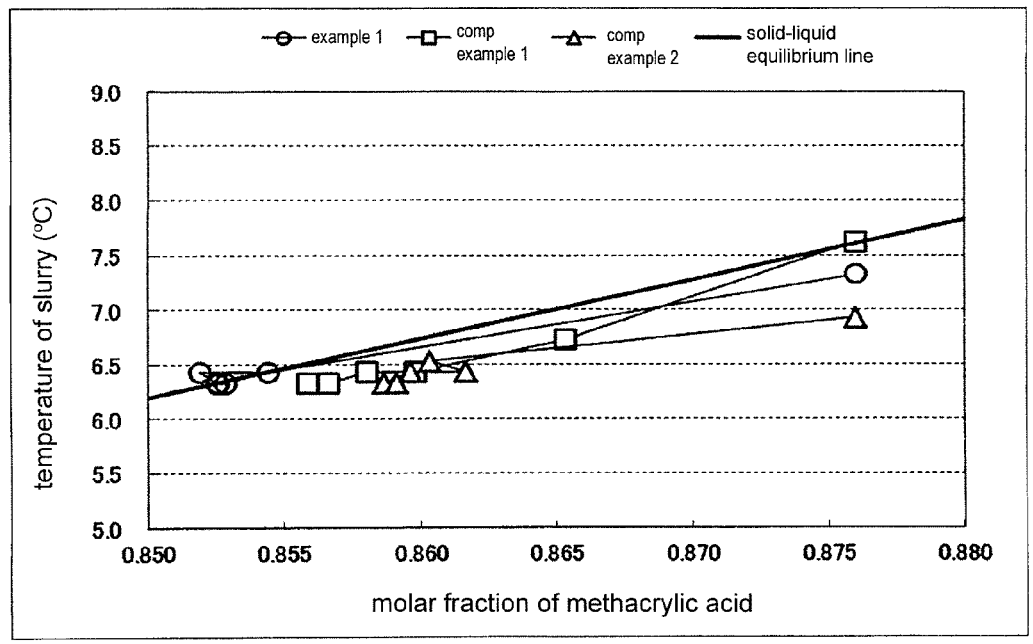
FIG. 1 is a graph showing slurry temperatures corresponding to molar fractions of methacrylic acid in example 1, comparative example 1, and comparative example 2.

In a method for purifying methacrylic acid according to an embodiment of the present invention, crystallization of methacrylic acid is performed by using crude methacrylic acid as a raw material with a maleic acid concentration of no greater than 2000 ppm by mass and an acrylic acid concentration of no greater than 2000 ppm by mass while setting a slurry temperature at −10~10° C.

The inventors of the present invention have conducted intensive studies and found that the productivity of methacrylic acid crystals is significantly affected by the maleic acid concentration and acrylic acid concentration in crude methacrylic acid as the raw material used for a crystallization procedure. Also, by controlling the slurry temperature during the crystallization process, it is found that scaling on the heat transfer surface and a decrease in the stirability of the slurry are prevented and the productivity of methacrylic acid crystals is enhanced. In addition, according to the present invention, highly purified methacrylic acid crystals are obtained at high productivity without enhancing cooling capacity more than necessary. In the following, embodiments of the present invention are described in detail. However, the present invention is not limited to those embodiments.

In an embodiment of the present invention, crude methacrylic acid is used as a raw material for purification. Crude methacrylic acid is produced by various methods such as a direct oxidization method and an ACH method. In a direct oxidization method, for example, at least one compound selected from a group of isobutylene, tert-butyl alcohol, methacrolein and isobutyl aldehyde is oxidized through single-stage or two-stage catalytic gas-phase oxidation reactions in the presence of molecular oxygen. Then, an organic solvent is used to extract methacrylic acid from a gas-condensate liquid obtained by condensing the reactant gas or a methacrylic acid solution obtained by adding water to the gas-condensate liquid or when the reactant gas is absorbed in water. By distilling the extracted liquid, the organic solvent and nonvolatile components are removed and crude methacrylic acid is obtained. When using an ACH method, for example, crude methacrylic acid is obtained by isolating the resultant byproduct of methacrylic acid through extraction or distillation.

Crude methacrylic acid indicates methacrylic acid containing impurities to be removed by a purification method related to the present invention. In addition, even if methacrylic acid has been already purified by rectification or crystallization, as long as it contains impurities that are to be removed by a method according to an embodiment of the present invention, it is also referred to as crude methacrylic acid as a purification target of the present invention.

As a raw material used in the method according to an embodiment of the present invention, crude methacrylic acid contains trace impurities such as maleic acid at a concentration of no greater than 2000 ppm by mass and acrylic acid at a concentration of no greater than 2000 ppm by mass. If concentrations of the trace impurities exceed the above range, the apparent solid-liquid equilibrium temperature of methacrylic acid is lowered, and the amount of deposited crystals from a saturated solution at the same cooling temperature is reduced. Also, due to the inhibiting effects of impurities, the amount of crystals produced within a certain period of time, namely, the crystal deposition rate, is lowered, and the productivity of methacrylic acid crystals decreases. The maleic acid concentration in crude methacrylic acid is preferred to be no less than 0 ppm by mass and no greater than 1500 ppm by mass, more preferably no less than 0 ppm by mass and no greater than 1000 ppm by mass, and even more preferably no less than 0 ppm by mass and no greater than 500 ppm by mass. The acrylic acid concentration in crude methacrylic acid is preferred to be no less than 0 ppm by mass and no greater than 1500 ppm by mass, more preferably no less than 0 ppm by mass and no greater than 1000 ppm by mass, and even more preferably no less than 0 ppm by mass and no greater than 500 ppm by mass. In addition, at least either the maleic acid concentration or the acrylic acid concentration in crude methacrylic acid may be set at 0 ppm by mass.

The maleic acid concentration is measured by high performance liquid chromatography (main body: brand name HP 1100, made by Agilent Technologies Inc., detector column: brand name CAPCELLPAK C18, made by Shiseido Co., Ltd.). The acrylic acid concentration is measured by gas chromatography (main body: brand name GC-17A, made by Shimadzu Corporation, detector column: brand name HP-FFAP, made by Agilent Technologies Inc.).

If at least either the maleic acid concentration or the acrylic acid concentration in crude methacrylic acid exceeds the concentration range for a raw material used in the present embodiment, such a concentration is adjusted by distillation, extraction or the like before the purification process is performed so that the maleic acid concentration and acrylic acid concentration are set within the concentration range related to the present invention. Since generally obtained crude methacrylic acid contains maleic acid and acrylic acid at a higher concentration than the concentration range related to the present invention, it is preferred to reduce the maleic acid concentration and the acrylic acid concentration in the crude methacrylic acid by employing at least either distillation or extraction before the purification process.

In addition to maleic acid and acrylic acid, crude methacrylic acid may contain impurities such as formic acid, acetic acid, propionic acid, citraconic acid, benzoic acid, toluic acid, terephthalic acid, formaldehyde, acetaldehyde, propionaldehyde, methacrolein, benzaldehyde, tolualdehyde and furfural. Other than maleic acid and acrylic acid, the total concentration of impurities contained in crude methacrylic acid is preferred to be no greater than 7000 ppm by mass, more preferably no greater than 5000 ppm by mass, and even more preferably no greater than 3000 ppm by mass. The total concentration of the impurities is measured by gas chromatography (main body: brand name GC-17A, made by Shimadzu Corporation, detector column: brand name HP-FFAP, made by Agilent Technologies Inc.).

For crystallization, one, two or more polar organic substances may also be mixed as a second component in crude methacrylic acid as a raw material. Combining a polar organic substance as a second component is preferable, since the crystallization processability is enhanced.

As for a polar organic substance as a second component, it is not limited to a specific type, as long as it does not form a solid solution with methacrylic acid when crystallization is performed. Examples of such polar organic substances are methanol, ethanol, propanol, butanol, diethyl ether, dioxane, tetrahydrofuran, acetone, methyl ethyl ketone, methyl isobutyl ketone, methyl formate, ethyl formate, methyl acetate, ethyl acetate, methyl methacrylate, ethyl methacrylate, methyl acrylate, ethyl acrylate and the like. Among those, a compound selected from a group of methanol, methyl methacrylate and methyl acrylate as a polar organic substance is preferred. As a polar organic substance, such a compound may be used alone or in any combination thereof.

In a total 100 mass % of crude methacrylic acid and a second component, the amount of the second component to be added to crude methacrylic acid is preferred to be 1 to 35 mass %, more preferably 3 to 30 mass %, even more preferably 3 to 10 mass %. When the amount of a second component is 1 mass % or greater, the temperature difference increases between the temperature at which methacrylic acid starts crystallizing, that is, the crystal deposition temperature of methacrylic acid, and the freezing point of methacrylic acid, thereby making it easier to conduct the crystallization process. In addition, by setting the added amount of a second component at 35 mass % or lower, a significant decrease in the crystal deposition temperature does not occur, and cooling does not require much energy or cost.

From the viewpoint of crystallization processability, the type and amount of a second component to be added are preferred to be selected so that the crystal deposition temperature of a mixed solution containing the second component will be within a range of −10~10° C., more preferably −2~10° C., even more preferably 3~10° C. The amount of a second component to be added is determined by obtaining solid-liquid equilibrium data of methacrylic acid and the second component. The crystal deposition temperature indicates a retained temperature of the slurry if the crystallization process is continuous, and indicates the slurry temperatures from the initial temperature of crystallization by cooling to the final attained temperature if the crystallization process is a batch type. Deposition of crystals can be visually confirmed.

When a mixed solution prepared by combining a second component into crude methacrylic acid is put through a crystallization process, maleic acid and acrylic acid concentrations determined in the present embodiment indicate the maleic acid and acrylic acid concentrations based on the amount of the crude methacrylic acid that excludes the second component.

The crystallization device used in the method related to the present invention is not limited to any specific type. Examples are those devices described in "Chemical Engineering Handbook, Revised, Sixth Edition," Maruzen Publishing Co., Ltd., 1999, pages 489-523. In addition, a backmixing column crystallizer (BMC), made by Nippon Steel Chemical Co., Ltd., Japan; a cooling disk crystallizer (CDC), made by Gouda, Netherlands; a falling film crystallizer (FFC), made by Sulzer Chemtech Ltd., Switzerland; and the like may also be used. Especially preferred is a suspension type jacket-cooled crystallization vessel (stirred-vessel crystallizer) equipped with a mixing vessel and a cooling device with a cooling jacket that wraps the external circumferential surface of the mixing vessel so that the cooling medium makes contact with the outer side of the vessel. Using the circumferential surface of the mixing vessel as the heat transfer surface, the inside of the mixing vessel is cooled through heat transfer, and the suspended crystal slurry is kept in the mixing vessel. In the method related to the present invention, a crystallization process may be conducted continuously or by batch.

The aforementioned crude methacrylic acid (a mixed solution with a polar organic solvent combined as a second component as needed) is put into a crystallization vessel of the crystallization device above, and cooled so that methacrylic acid crystals are deposited (crystallization process). Accordingly, a slurry with methacrylic acid crystals is obtained. It is preferred to keep stirring the slurry when the solution is cooled.

In the present embodiment, the slurry temperature in the crystallization vessel during the crystallization process is −10~10° C. The slurry temperature is preferred to be −2~10° C., more preferably 0~10° C., and even more preferably 3~10° C. If the slurry temperature is lower than −10° C., not only does the amount of crystals in the slurry become too much, but also generation of microcrystals is observed as the crystals collides and crushes with each other. Accordingly, the processability of the obtained slurry is lowered, causing an increase in the amount of the mother liquor adhered to the crystal surfaces after solid-liquid separation. On the other hand, if the slurry temperature exceeds 10° C., the amount of crystals in the slurry decreases, lowering productivity. Here, the slurry temperature indicates the retained temperature of the slurry when the crystallization process is continuous and the final attained temperature of the slurry when the crystallization is processed by batch.

When a suspension type jacket-cooled crystallization vessel is used as a crystallization device, the absolute value (maximum) of the difference between the crystal deposition temperature and the temperature of the cooling medium in the jacket is preferred to be 15° C. or lower, more preferably 10° C. or lower, even more preferably 7° C. or lower. By setting the absolute value of the difference at 15° C. or lower between the crystal deposition temperature and the temperature of the cooling medium in the jacket, excessive supersaturation at the heat transfer surface is prevented, while scaling on the heat transfer surface is prevented. Also, the generation of microcrystals is suppressed, thereby enhancing the processability of the obtained slurry and decreasing the amount of the mother liquor adhered to the crystal surfaces after solid-liquid separation.

Next, the obtained slurry is separated into methacrylic acid crystals and the mother liquor. Accordingly, purified methacrylic acid crystals are achieved. Meanwhile, the separated mother liquor generally contains concentrated impurities, methacrylic acid, and the second component if a second component is added.

The method for separating methacrylic acid crystals and the mother liquor is not limited specifically as long as the solid and the liquid are separated. For example, widely known solid-liquid separators such as filtration devices and centrifugal separators as well as any combination thereof may be used. A specific example of separation devices is a Kureha Crystal Purifier (KCP) as seen in "Purification of Organic Compound by Kureha Continuous Crystal Purifier," by Chuzo Shimizu, Chemical Engineering, Volume 27, Issue 3 (1982), page 49. The separation process may be conducted continuously or by a batch method.

Methacrylic acid and the second component are recovered from the separated mother liquor and then are recycled or put through the purification process again. The methacrylic acid recovered from the mother liquor may be used as raw material for producing methacrylic acid esters through esterification reactions. Here, as the raw material for producing methacrylic acid esters, the separated mother liquor can be used as is. Thus, from an economical point of view, the mother liquor is preferred to be used without being purified again. When esters are produced using the separated mother liquor, raw materials such as alcohol and/or methacrylic acid may further be added to the mother liquor. In addition, when the separated mother liquor is recycled as a raw material for crystallization, crude methacrylic acid is added so that the maleic acid concentration is no greater than 2000 ppm by mass and the acrylic acid concentration is no greater than 2000 ppm by mass in the raw material based on the amount that excludes a second component. Alternatively, the mother liquor may also be recycled after the maleic acid and acrylic acid concentrations in the mother liquor are reduced through a separation process such as distillation, crystallization, extraction or the like.

The following is an example of the method for calculating the amount of deposited crystals in the purification when methanol is used as a second component. The following method may also be used when a component other than methanol is used or when no second component is used. First, it is assumed that neither methacrylic acid and methanol nor methacrylic acid and maleic acid form a solid solution (that is, the entire amount of methanol and maleic acid exist in the mother liquor), and the amount of deposited crystals is calculated from Formulas (1) and (2) below.

Formula 1

$$W_C = W_{MAA0} - W_{MAA} \quad (1)$$

[Formula 2]

$$W_{MAA} = \frac{W_{MeOH}}{C_{MeOH}} - W_{MeOH} - W_{MAL\text{-}A} \quad (2)$$

In Formulas (1) and (2), "$W_C$" is the deposited amount [g] of methacrylic acid crystals, "$W_{MAA0}$" is the initial amount of methacrylic acid [g], "$W_{MAA}$" is the amount [g] of methacrylic acid in the mother liquor, "$W_{MeOH}$" is the amount [g] of methanol in the mother liquor, "$W_{MAL\text{-}A}$" is the amount [g] of maleic acid in the mother liquor, and "$C_{MeOH}$" is the concentration [mass fraction] of methanol in the mother liquor.

Regarding the driving force of crystallization, when it is thought to be derived from the difference between the amount of crystals deposited from saturated methacrylic acid and the concentration of methacrylic acid in the mother liquor with respect to the slurry temperature, Formula (3) below is formulated. Formula (4) below is obtained by integrating Formula (3). Using the amount of deposited crystals by sampling during the purification process, parameter fitting is carried out for "K" and "w*" in Formula (4) below by a least-squares method. Using the fitted parameters, the chronological change in the amount of deposited crystals is calculated.

Formula 3

$$\frac{dw_c}{d\theta} = K \frac{w_c^* - w_c}{w_c^*} \quad (3)$$

Formula 4

$$w_c = w_c^* - w_c^* \exp\left(-\frac{K\theta}{w_c^*}\right) \quad (4)$$

In Formulas (3) and (4) above, "$w_C$" is the amount [g] of deposited methacrylic acid crystals, "θ" is elapsed time [s], "K" is the crystal deposition rate constant [g/s], and "$w^*_C$" is the amount [g] of crystals deposited from saturated methacrylic acid.

In the present embodiment, the crystal deposition rate constant "K" defined in Formula (4) above is preferred to be 1.5 times the constant when the maleic acid concentration is 6300 ppm by mass, from the productivity point of view of methacrylic acid crystals.

EMBODIMENTS

In the following, the present invention is described in detail by listing examples. However, the present invention is not limited to those examples.

In each example and comparative example, a crystallization process was conducted by employing a batch method and using a suspension type jacket-cooled glass crystallization vessel (140 mL) equipped with a mixing mechanism. As for a cooling medium, Etabrine EC-Z (brand name, made by Tokyo Fine Chemical Co., Ltd.) was used.

The concentration of a component except for maleic acid was measured by using gas chromatography (main body: brand name GC-17A, made by Shimadzu Corp., detector column: brand name HP-FFAP, made by Agilent Technologies Inc.). The concentration of maleic acid was measured by using high performance liquid chromatography (main body: brand name HP 1100, made by Agilent Technologies Inc., detector column: brand name CAPCELLPAK C18, made by Shiseido Co., Ltd.). The detection limit of propionic acid is 10 ppm by mass, the detection limit of maleic acid is 10 ppm by mass, the detection limit of acrylic acid is 10 ppm by mass, and the detection limit of tolualdehyde is 300 ppm by mass.

Example 1

Using a direct oxidation method, tert-butyl alcohol was reacted through catalytic gas-phase oxidation in the presence of molecular oxygen. The obtained reactant gas was absorbed in water, and an organic solvent was used to extract methacrylic acid from the prepared methacrylic acid solution. By distilling the extract, the organic solvent and nonvolatile components were removed, and 57.0 grams of crude methacrylic acid (A) containing the impurities shown in Table 1 was used as a raw material.

TABLE 1

| type of impurity | impurity concentration (ppm by mass) |
| --- | --- |
| propionic acid | 9 |
| maleic acid | not detected |
| acrylic acid | 180 |
| tolualdehyde | not detected |

A mixed solution of the aforementioned crude methacrylic acid (A) and 3.0 grains of methanol (second component) were put into the aforementioned suspension type jacket-cooled glass crystallization vessel and retained at 15~20° C. while being stirred with a small stirring bar.

The aforementioned cooling medium was circulated in the jacket (temperature set at 6.0° C.), and the mixed solution in the crystallization vessel was cooled for 120 minutes. The solution temperature in the crystallization vessel was chronologically measured using a type K thermocouple. Two minutes after circulation started and when the temperature of the mixed solution had reached 7.4° C., crystals were deposited. After 120 minutes had elapsed, the final attained temperature of the slurry in the crystallization vessel was 6.3° C. and no scaling was observed on the heat transfer surface. The absolute value of the difference between the crystal deposition temperature and the temperature of the cooling medium in the jacket was 1.3° C. at maximum. The temperature of the cooling medium in the jacket was lower than the crystal deposition temperature in all the examples and comparative examples. Also, a sample of approximately 1 mL was taken from the mother liquor in the crystallization vessel every predetermined time to measure the methanol concentration in the mother liquor. Table 2 shows chronological changes in the molar fraction of methacrylic acid in the mother liquor and slurry temperature in the crystallization vessel. In addition, FIG. 1 is a graph showing the slurry temperature with respect to a molar fraction of methacrylic acid. The molar fractions of methacrylic acid in Table 2 and FIG. 1 were calculated by subtracting the amount of methanol from the total amount of mother liquor.

Figure 2:
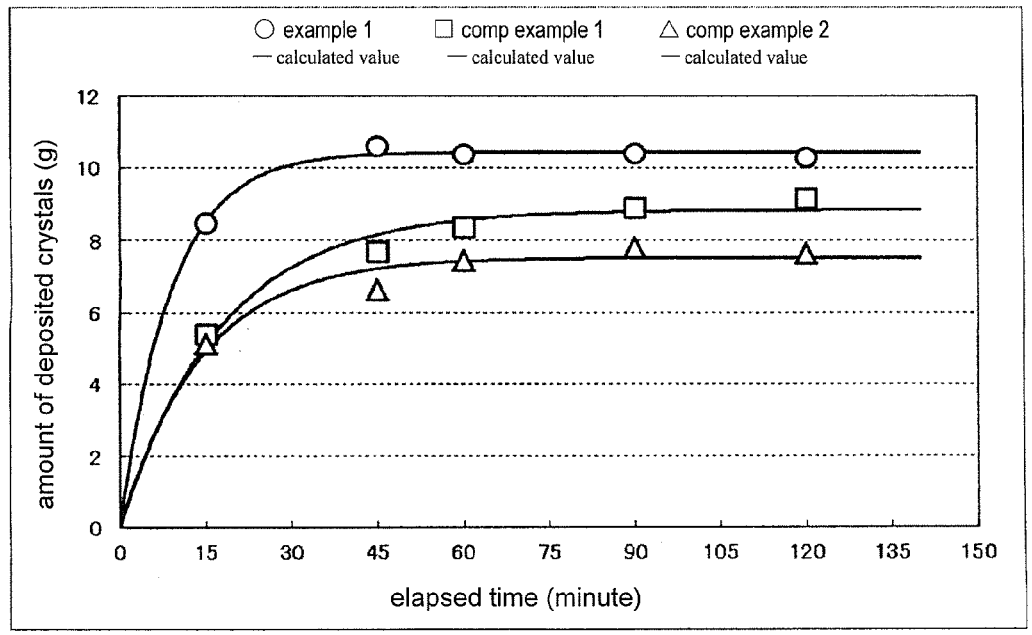
FIG. 2 is a graph showing chronological changes in the amount of deposited crystals in example 1, comparative example 1, and comparative example 2.

Next, assuming that neither methacrylic acid and methanol nor methacrylic acid and maleic acid form a solid solution (that is, entire amounts of methanol and maleic acid are present in the mother liquor), the amount of deposited crystals was calculated using Formulas (1) and (2) above. FIG. 2 shows chronological change in the amount of deposited crystals. When calculating molar fractions of methacrylic acid in Table 2 and FIG. 1, and in Formulas (1) and (2) above, the reduction of the solution caused by sampling was considered.

Figure 3:
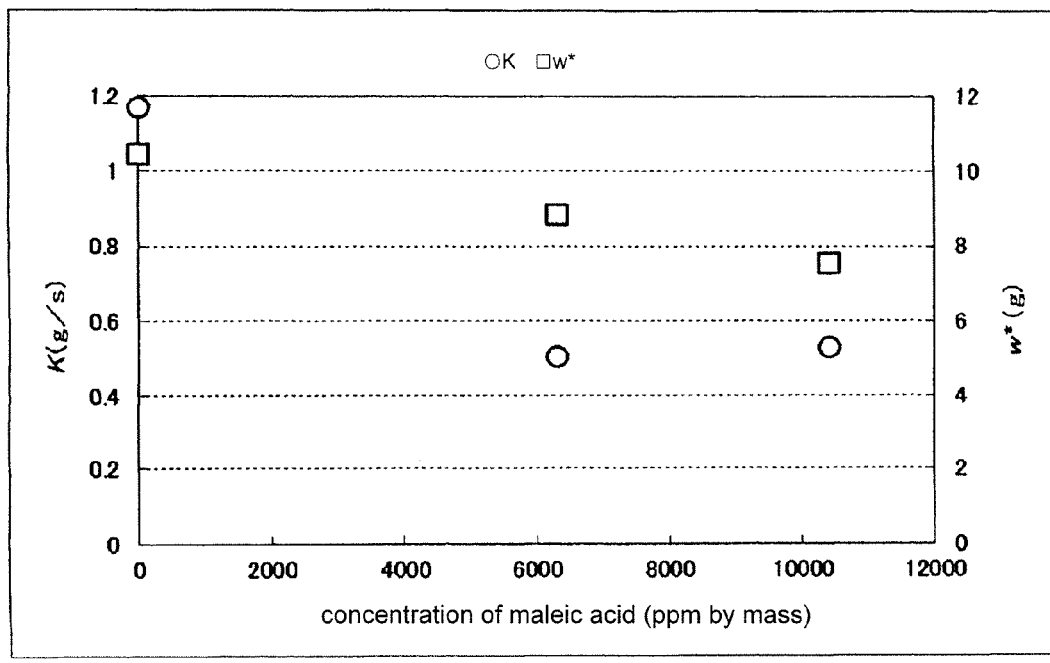
FIG. 3 is a graph showing crystal deposition rate constants (K) and the amounts of deposited crystals (w*) from saturated methacrylic acid with respect to the maleic acid concentration in a mixed solution of example 1, comparative example 1, and comparative example 2.

Next, using the amount of deposited crystals obtained by sampling during the purification process, parameter fitting was carried out for "K" and "w*" in Formula (4) below by a least-squares method. Values "K" and "w*" with respect to the maleic acid concentration are shown in FIG. 3. Also, FIG. 2 shows the chronological change in the amount of deposited crystals calculated by using the fitted parameters.

Comparative Example 1

As the raw material, crude methacrylic acid (B) was prepared by mixing 0.36 grams of maleic acid into 57.0 grams of crude methacrylic acid (A) in Example 1 (maleic acid concentration: 6300 ppm by mass; acrylic acid concentration: 180 ppm by mass). The crystallization process was conducted the same as in Example 1 except that a mixed solution of crude methacrylic acid (B) and 2.9 grams of methanol (second component) was used. The added amount of methanol was set so that the methacrylic acid concentration in the mixed solution (based on molar fraction) is the same as the methacrylic acid concentration of the mixed solution in Example 1.

Two minutes after the start of circulation and when the mixed solution temperature had reached 7.8° C., crystals were deposited. After 120 minutes had elapsed, the final attained temperature of the slurry in the crystallization vessel was 6.3° C. and no scaling was observed on the heat transfer surface. The absolute value of the difference between the crystal deposition temperature and the temperature of the cooling medium in the jacket was 1.6° C. at maximum. Table 2 shows chronological change in the molar fraction of methacrylic acid in the mother liquor and slurry temperature in the crystallization vessel. FIG. 1 is a graph showing the slurry temperature with respect to the molar fraction of methacrylic acid. FIG. 2 shows chronological change in the amount of deposited crystals. FIG. 3 shows values of "K" and "w*" with respect to maleic acid concentrations. Also, FIG. 2 shows chronological change in the amount of deposited crystals calculated using the parameters. The molar fractions of methacrylic acid in Table 2 and FIG. 1 were calculated by subtracting the amount of methanol and maleic acid from the total amount of mother liquor.

Comparative Example 2

As the raw material, crude methacrylic acid (C) was prepared by mixing 0.6 grams of maleic acid into 57.0 grams of crude methacrylic acid (A) in Example 1 (maleic acid concentration: 10400 ppm by mass; acrylic acid concentration: 180 ppm by mass). The crystallization process was conducted the same as in Example 1 except that a mixed solution of crude methacrylic acid (C) and 2.8 grams of methanol (second component) was used. The added amount of methanol was set so that the methacrylic acid concentration in the mixed solution (based on molar fraction) was the same as the methacrylic acid concentration of the mixed solution in Example 1.

Three minutes after the start of circulation and when the mixed solution temperature had reached 6.9° C., crystals were deposited. After 120 minutes had elapsed, the final attained temperature of the slurry in the crystallization vessel was 6.3° C. and no scaling was observed on the heat transfer surface. The absolute value of the difference between the crystal deposition temperature and the temperature of the cooling medium in the jacket was 0.9° C. at maximum. Table 2 shows chronological change in the molar fraction of methacrylic acid in the mother liquor and slurry temperature in the crystallization vessel. FIG. 1 is a graph showing the slurry temperature with respect to the molar fraction of methacrylic acid. FIG. 2 shows chronological change in the amount of deposited crystals. FIG. 3 shows values of "K" and "w*" with respect to maleic acid concentrations. Also, FIG. 2 shows chronological change in the amount of deposited crystals calculated using the parameters. The molar fractions of methacrylic acid in Table 2 and FIG. 1 were calculated by subtracting the amount of methanol and maleic acid from the total amount of mother liquor.

TABLE 2

| | example 1 | | comparative example 1 | | comparative example 2 | |
|---|---|---|---|---|---|---|
| time (min) | methacrylic acid molar fraction | temperature (° C.) | methacrylic acid molar fraction | temperature (° C.) | methacrylic acid molar fraction | temperature (° C.) |
| 3 | 0.876 | 7.3 | 0.876 | 7.6 | 0.876 | 6.9 |
| 15 | 0.858 | 6.6 | 0.865 | 6.7 | 0.865 | 6.7 |
| 45 | 0.852 | 6.4 | 0.860 | 6.4 | 0.862 | 6.4 |
| 60 | 0.853 | 6.3 | 0.858 | 6.4 | 0.860 | 6.4 |
| 90 | 0.853 | 6.3 | 0.857 | 6.3 | 0.859 | 6.3 |
| 120 | 0.853 | 6.3 | 0.856 | 6.3 | 0.859 | 6.3 |

From Table 2, and FIGS. 1 and 2, it is found that in Comparative Examples 1 and 2 in which the maleic acid concentration in the crude methacrylic acid solution exceeds 2000 ppm by mass, the rate at which the mother liquor composition in the crystallization vessel reaches equilibrium, namely, the crystal deposition rate, is slower than that in Example 1 in which the maleic acid concentration in the crude methacrylic acid is no greater than 2000 ppm by mass. Also, it is found that the amount of crystals obtained 120 minutes after the start of crystallization was smaller in Comparative Examples 1 and 2 than that in Example 1.

As shown in FIG. 3, it is found that the apparent solid-liquid equilibrium temperature of methacrylic acid is lowered and that the amount of deposited crystals (w*) from saturated methacrylic acid was reduced at the same cooling temperature (6.3° C.) in Comparative Examples 1 and 2 compared with Example 1. Moreover, it is also found that due to the inhibiting effects of impurities, the amount of crystals obtained in a certain period of time, namely, the crystal deposition rate, is lowered, thereby decreasing the productivity of methacrylic acid crystals.

Example 2

Methacrolein was reacted with molecular oxygen under catalytic gas-phase oxidation. After the obtained purified reactant gas was condensed and extracted, crude methacrylic acid (D) was obtained through distillation. The components contained in crude methacrylic acid (D) were analyzed, and the impurities shown in Table 3 were contained.

TABLE 3

| type of impurity | impurity concentration (ppm by mass) |
|---|---|
| propionic acid | 177 |
| maleic acid | 2522 |
| acrylic acid | 2163 |
| tolualdehyde | 250 |

Crude methacrylic acid (D) was further distilled to obtain crude methacrylic acid (E). The components contained in crude methacrylic acid (E) were analyzed, and the impurities shown in Table 4 were identified.

TABLE 4

| type of impurity | impurity concentration (ppm by mass) |
|---|---|
| propionic acid | 20 |
| maleic acid | not detected |
| acrylic acid | 112 |
| tolualdehyde | not detected |

As the raw material, 57.0 grams of crude methacrylic acid (E) was used. A mixed solution of crude methacrylic acid (E) and 3.0 grams of methanol (second component) were put into the aforementioned suspension type jacket-cooled glass crystallization vessel and retained at 20~25° C. while being stirred using a small stirring bar.

The aforementioned cooling medium was circulated in the jacket (temperature set at 6.0° C.), and the mixed solution in the crystallization vessel was cooled for 60 minutes. The solution temperature in the crystallization vessel was chronologically measured using a resistance temperature detector (Pt-100). Five minutes after the start of circulation and when the temperature of the mixed solution had reached 7.7° C., crystals were deposited. The final attained temperature of the slurry in the crystallization vessel was 6.6° C. after 60 minutes, and no scaling was observed on the heat transfer surface. The absolute value of the difference between the crystal deposition temperature and the temperature of the cooling medium in the jacket was 1.7° C. at maximum.

Next, suction filtration was conducted on the obtained slurry for 30 seconds in a cooler with the ambient temperature set at 10° C. using an aspirator. Accordingly, methacrylic acid crystals (E) were obtained. Table 5 shows the recovery rate of methacrylic acid calculated by dividing the obtained amount of crystals by the amount of methacrylic acid supplied into the vessel. Also, when components of obtained methacrylic acid crystals (E) were analyzed, the impurities shown in Table 6 were identified. An analysis of maleic acid in methacrylic acid crystals (E) was not conducted.

Comparative Example 3

As the raw material, 57.0 grams of crude methacrylic acid (D) in Example 2 was used. The crystallization process was conducted the same as in Example 2 except that a mixed solution of crude methacrylic acid (D) and 3.0 grams of methanol (second component) was used. Seven minutes after the start of circulation and when the temperature of the mixed solution had reached 6.7° C., crystals were deposited. The final attained temperature of the slurry in the crystallization vessel was 6.6° C. after 60 minutes, and no scaling was observed on the heat transfer surface. The absolute value of the difference between the crystal deposition temperature and the temperature of the cooling medium in the jacket was 0.7° C. at maximum.

Next, methacrylic acid crystals (D) were obtained by the same procedure as in Example 2. Table 5 shows the recovery rate of methacrylic acid calculated by dividing the obtained amount of crystals by the amount of methacrylic acid supplied into the vessel. Also, when components of obtained methacrylic acid crystals (D) were analyzed, impurities shown in Table 6 were identified. The analysis of maleic acid in methacrylic acid crystals (D) was not conducted.

TABLE 5

| | methacrylic acid recovery rate (%) |
|---|---|
| example 2 | 24.5 |
| comparative example 3 | 14.3 |

TABLE 6

| | concentration of impurity (ppm by mass) | |
|---|---|---|
| type of impurity | example 2 (methacrylic acid crystal (E)) | comparative example 3 (methacrylic acid crystal (D)) |
| propionic acid | not detected | 90 |
| acrylic acid | 20 | 580 |
| tolualdehyde | not detected | 990 |

From Table 5, when a raw material is such a crude methacrylic acid in which the maleic acid concentration exceeds 2000 ppm by mass and the acrylic acid concentration exceeds 2000 ppm by mass, it is found that the amount of methacrylic acid crystals obtained in a certain period of time, namely, the productivity, is lowered.

Comparative Example 4

The same crystallization process was conducted as in Example 2 except that the temperature of the cooling medium to be circulated in the jacket was set at −20° C. Two minutes after the start of circulation and when the temperature of the mixed solution had reached 7.8° C., crystals were deposited. After 15 minutes had elapsed and when the final attained temperature of the slurry in the crystallization vessel was −12° C., a significant amount of scaling was observed on the heat transfer surface and the slurry concentration in the crystallization vessel was too high to stir. Thus, the crystallization process was stopped. The absolute value of the difference between the crystal deposition temperature and the temperature of the cooling medium in the jacket was 28.5° C. at maximum.

From the results above, it is found that when the slurry temperature is outside the range of −10~10° C., not only does scaling progress on the heat transfer surface but also the processability of the obtained slurry decreases.

The invention claimed is:
1. A method for purifying methacrylic acid, comprising:
crystallizing methacrylic acid, using crude methacrylic acid as a raw material having a maleic acid concentration of no greater than 2000 ppm by mass and an acrylic acid concentration of no greater than 180 ppm by mass, and setting a slurry temperature at −10~10° C., wherein a suspension-type jacked-cooled crystallization vessel is used as a crystallization device, and an absolute value of the difference between a crystal deposition temperature and a temperature of a cooling medium in the jacket is set at 15° C. or lower.

2. The method for purifying methacrylic acid according to claim 1, wherein a crystal deposition rate constant "K" defined in Formula (4) below is set to be 1.5 times the constant when the maleic acid concentration is 6300 ppm by mass:

$$w_c = w_c^* - w_c^* \exp\left(-\frac{K\theta}{w_c^*}\right), \quad (4)$$

wherein in Formula (4), "$w_C$" is the amount [g] of deposited methacrylic acid crystals, "$\theta$" is elapsed time [s], "K" is the crystal deposition rate constant [g/s], and "$w^*_C$" is the amount [g] of crystals deposited from saturated methacrylic acid.

3. The method for purifying methacrylic acid according to claim 1, further comprising reducing the maleic acid concentration and the acrylic acid concentration in the crude methacrylic acid by conducting at least distillation or extraction before performing a purification process.

4. The method for purifying methacrylic acid according to claim 1, wherein a total concentration of impurities calculated by excluding maleic acid and acrylic acid contained in the crude methacrylic acid is set to be no greater than 7000 ppm by mass.

5. The method for purifying methacrylic acid according to claim 2, further comprising reducing the maleic acid concentration and the acrylic acid concentration in the crude methacrylic acid by conducting at least distillation or extraction before performing a purification process.

6. The method for purifying methacrylic acid according to claim 2, wherein a total concentration of impurities calculated by excluding maleic acid and acrylic acid contained in the crude methacrylic acid is set to be no greater than 7000 ppm by mass.

7. The method for purifying methacrylic acid according to claim 3, wherein a total concentration of impurities calculated by excluding maleic acid and acrylic acid contained in the crude methacrylic acid is set to be no greater than 7000 ppm by mass.

* * * * *